United States Patent
Carmosin et al.

[11] Patent Number: 5,541,217
[45] Date of Patent: Jul. 30, 1996

[54] 4-ARYLCYCLOPENTA[C]PYRROLE ANALGESICS

[75] Inventors: Richard J. Carmosin, Quakertown; John R. Carson, Norristown; Philip M. Pitis, North Wales, all of Pa.

[73] Assignee: Ortho Pharmaceutical Corporation, Raritan, N.J.

[21] Appl. No.: 443,142

[22] Filed: May 17, 1995

[51] Int. Cl.$^6$ ........................ A61K 31/395; C07D 209/02
[52] U.S. Cl. ........................ 514/412; 548/466; 548/515; 546/276.7
[58] Field of Search ........................ 548/466, 515; 546/272; 514/412, 414, 339

[56] References Cited

U.S. PATENT DOCUMENTS 5,216,018  6/1993  Ciganek ........................ 514/416

OTHER PUBLICATIONS

CA 114:6288u Preparation of . . . antibiotics. Ogata et al., p. 619, 1991.

*Primary Examiner*—Joseph K. McKane

[57] ABSTRACT

The 4-arylcyclopenta[c]pyrroles of the following formula are effective analgesics:

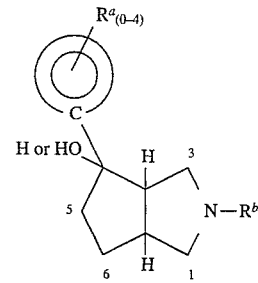

including stereoisomers and pharmaceutically acceptable salts thereof, wherein

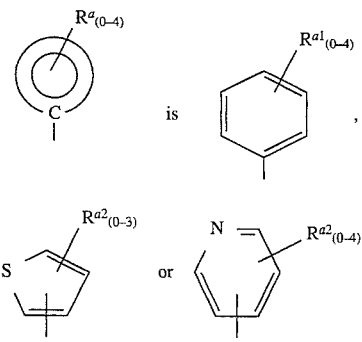

with the proviso that the 3a and 6a hydrogens are cis and where there is a 4-position hydroxy then such is trans to the 3a and 6a hydrogens, and with the proviso that $R^b$ is not hydrogen when the 4-position aryl is cis to the 3a and 6a hydrogens and there is no hydroxy at the 4-position.

13 Claims, No Drawings

4-ARYLCYCLOPENTA[C]PYRROLE ANALGESICS

The present invention relates to analgesics. More particularly, the present invention relates to 4-arylcyclopenta[c]pyrroles having analgesic activity.

BACKGROUND OF THE INVENTION

Analgesics used today in clinical practice suffer either from limited efficacy, limiting side effects or both. The non-steroidal antiinflammatory agents such as aspirin and ibuprofen fail to treat severe pain and cause gastrointestinal side effects. The opiates (morphine, codeine or meperidine) can treat more severe pain, but are subject to addiction liability and cause constipation and respiratory depression.

French Patent 8915407, to Rorer-Rhone Poulenc, discloses the compound:

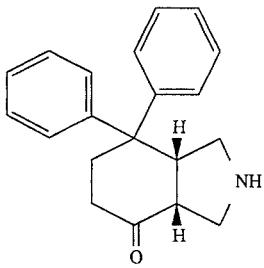

No biological utility is taught.

Eur. Pat. No. 430 771, to Rhone Poulenc, discloses the compound:

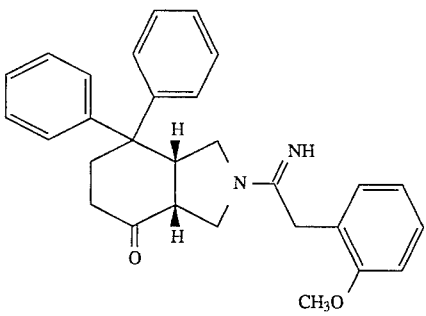

The biological utility is disclosed as a Substance P antagonist.

Ciba-Giegy has publicly disclosed the compound:

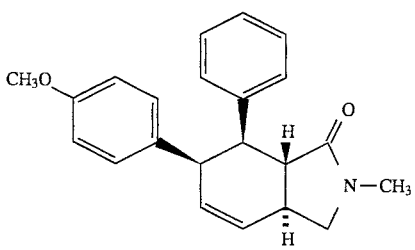

However, no biological activity was taught for this compound and its suitability for use as an analgesic is unknown.

U.S. Pat. No. 5,216,018, to Ciganek discloses isoindoles of the formula:

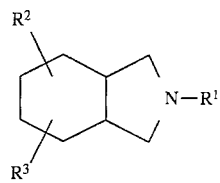

wherein $R^2$ and $R^3$ are disclosed among many other substituents to be independently phenyl. These compounds are disclosed as useful to treat physiological or drug induced psychosis and as antidyskinetic agents.

SUMMARY OF THE INVENTION

The present invention provides novel 4-arylcyclopenta[c]pyrroles having analgesic activity Of the formula:

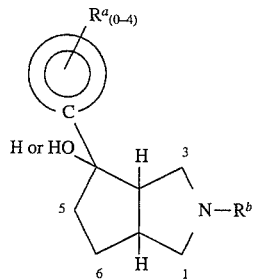

including the purified stereoisomers and pharmaceutically acceptable salts thereof,
wherein

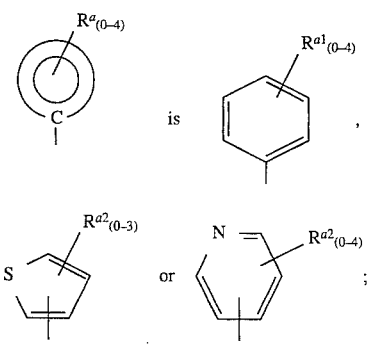

$R^{a1}$ is selected from the group consisting of halogen, $C_{1-4}$alkyl, substituted $C_{1-4}$alkyl (wherein the substituent is $C_{1-4}$alkoxy, hydroxy or perhalo), $C_{1-4}$alkoxy, substituted $C_{1-4}$alkoxy (wherein the substituent is perfluoro), di($C_{1-4}$alkyl)amino, $C_{1-4}$alkylsulfonyl and phenyl;

$R^{a2}$ is selected from the group consisting of halogen or $C_{1-4}$alkyl;

$R^b$ is selected from the group consisting of hydrogen, $C_{1-4}$alkyl, $C_{1-4}$alkenyl, $C_{1-6}$cycloalkylmethyl and $C_{1-6}$cycloalkyl;

with the proviso that the 3a and 6a hydrogens are cis and where there is a 4position hydroxy then such is trans to the 3a and 6a hydrogens, and with the proviso that $R^b$ is not hydrogen or $C_{1-4}$alkenyl when the 4-position aryl is cis to the 3a and 6a hydrogens and there is no hydroxy at the 4-position.

DETAILED DESCRIPTION OF THE INVENTION

The compounds of Formula (I) can be divided into two basic structures:

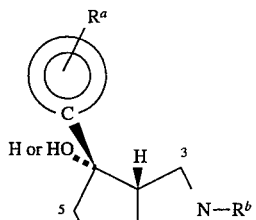

3aβ, 4β, 6aβ and
3aα, 4α, 6aα

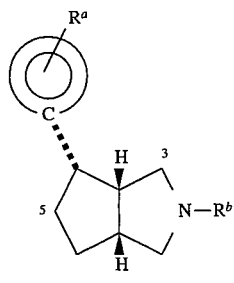

3aβ, 4α, 6aβ and
3aα, 4β, 6aα where $R^a$ and $R^b$ are as defined above. Unless specifically indicated otherwise, the structures herein represent the depicted stereoisomer as a racemic mixture.

Flow Sheets A, B and C illustrate the production of core 4-arylcyclopenta[c]pyrrole. In the Flow Sheets, the case in which the aryl is phenyl is exemplified. Each of the compounds represented by Formula I has three stereocenters and, in consequence, $2^3$ or 8 stereoisomers which include 4 diastereomers.

A: Synthesis of 4-hydroxy $1^a$

The 4-hydroxy $1^a$ of Flow Scheme A is obtained from commonly available starting materials which include cyclopentene-1-one, N-butoxymethyl-N-methyl-N'trimethylsilylmethylamine and phenyllithium. Of course, the equivalent lithiated pyddine or thiophene rather than phenyllithium would be employed in Flow Sheet A to obtain those alternate aryl moieties at the 4-position of the desired cyclopenta[c]pyrrole. The description herein using the phenyllithium is for exemplification only. In a first step, cyclopentene-1-one A1 is reacted with an azomethine ylide which results from the treatment of N-$C_{1-4}$alkoxymethyl-N-Rb-N-trimethylsilylmethylamine A2 with TFA in a literature cycloaddition of an azomethine ylide to an activated double bond to produce 2-Rb-3aα, 6aα-chexahydrocyclopenta[c]pyrrol-4(1H)one A3. This cycloaddition may be carried out in a halocarbon solvent at reflux by simply adding the two reactants and subsequently adding trifluoroacetic acid (TFA). The reaction was found to be sensitive to the manner and amount of trifluoroacetic acid addition. Herein, a 1% solution of TFA was added to the reflux dropwise until the cycloaddition was complete. Subsequently, the ketone A3 is reacted with the aryllithium by mixing the reactants in a solvent, such as, diethyl ether, THF or hexane and allowing the mixture to stir for 1–6 hours at from −78° C. to room temperature to produce 2-$R^b$-4α-phenyl-3aα,6aα-octahydrocyclopenta[c]pyrrol-4β-ol $1^a$.

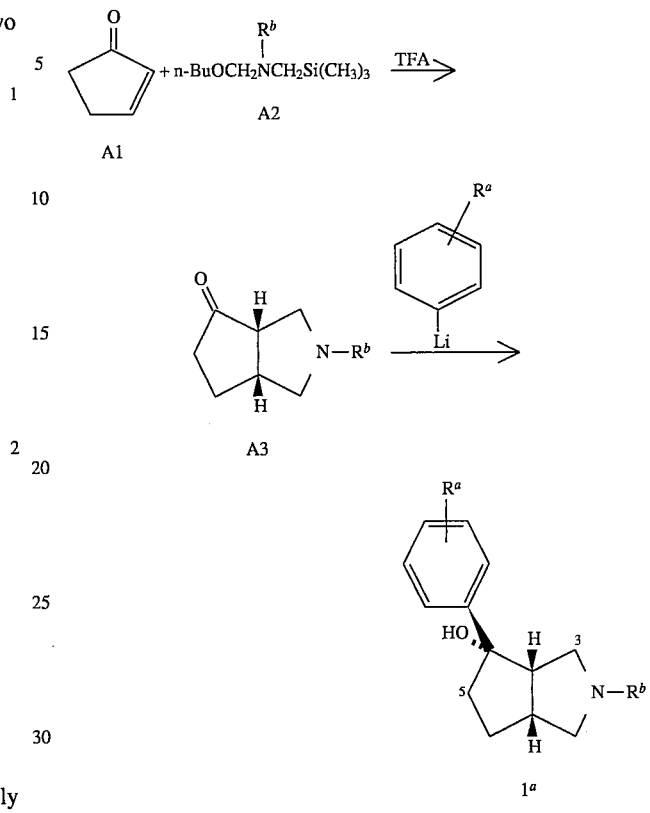

B: Synthesis of 2

Compounds 2 of Flow Scheme B is obtained from 4-hydroxy $1^a$. Of course, the equivalent 4-hydroxy $1^a$ with pyridine or thiophene rather than phenyl would be employed in Flow Sheet B as the starting material to obtain these alternate aryl moieties at the 4-position of the desired cyclopenta[c]pyrrole. The description herein using the phenyl bearing cyclopenta[c]pyrrole is for exemplification only. To obtain 2,4-hydroxy $1^a$ is subjected to hydrogenolysis over palladium in the presence of an acid. Alternatively, the transformation may be carried out by dehydration of $1^a$ to the 4,5-olefin caused by treatment with a protic acid followed followed by hydrogenation over Raney nickel or over a noble metal, such as, palladium, platinum, rhodium or nickel, with or without heat and at pressures from atmospheric to 100 psi. The acid in either case may be selected from acetic acid, perchloric acid, sulfuric acid or p-toluenesulfonic acid.

FLOW SCHEME B

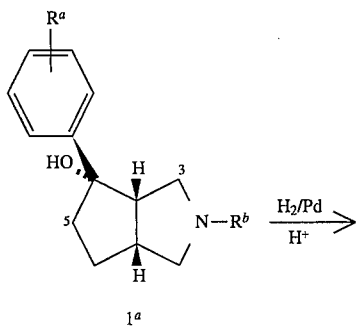

-continued
FLOW SCHEME B

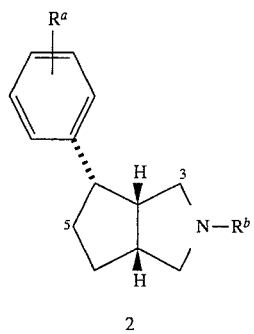

2

C: Synthesis of $1^b$

The description herein using the 3-phenyl compound is for exemplification only. Of course, the equivalent 3-thienyl or 3-pyridinyl rather than 3-phenylcyclopent-1-ene would be employed in Flow Sheet C to obtain those alternate aryl moieties at the 4-position of the desired cyclopenta[c]pyrrole. Initially, to produce the starting material C1, cyclopentenyl acetate is coupled with an arylzinc halide in the presence of palladium acetate to prepare arylcyclopentenes of type C1. Subsequently, cyclopent-1-ene C1 is reacted with an azomethine ylide which results from the treatment of trimethylamino-N-oxide C2 with LDA, in a literature cycloaddition of an azomethine ylide to a non-activated double bond to produce 2-methyl-4α-phenyl-3aα,6aα-octahydrocyclopenta[c]pyrrole C3. This cycloaddition may be carded out in a hydrocarbon solvent or THF in the presence of a strong base at from −78° C. to room temperature. The preferred base, lithium diisopropylamine (LDA), may be made form n-butyllithium and diisopropylamine.

FLOW SCHEME C

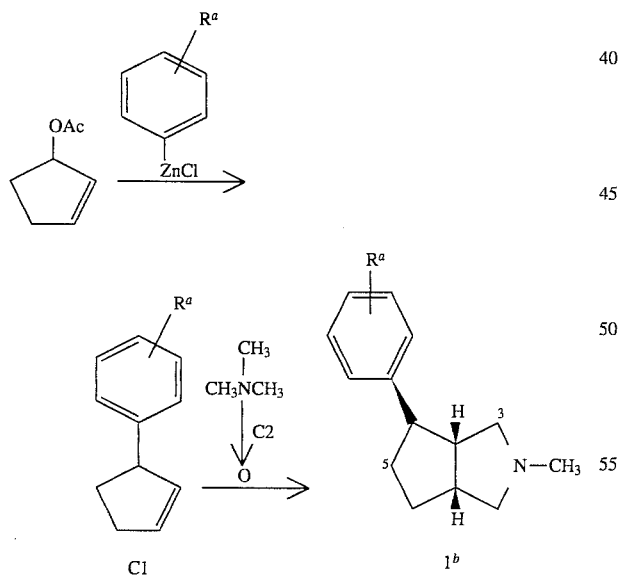

As seen, Flow Sheets A, B and C show the production of diastereomers. Each diastereomer may be separated into individual enantiomers using chiral HPLC techniques. Such techniques are well known in the art. Suitable columns on which chiral HPLC separations may be carried out are available on the market and include CYCLOBOND 1-2000, manufactured by ASTEC COMPANY of Whippany, N.J.

Alternatively, classical resolution employing a chiral acid may be used to produce individual enantiomers. Suitable chiral acids include D or L tartaric acids and D or L bromocamphorsulfonic acids.

The manufacture of starting materials described above is well known. Starting material A2 may be obtained by heating methylamine and chloromethyltrimethylsilane to produce N-methyl-N-trimethylsilylmethylamine and adding this material dropwise to a solution of aqueous formaldehyde followed by the addition of n-butanol and potassium carbonate. Analogous A2 such as N-benzyl and N-cyclohexyl may be similarly produced. Starting material A1 may be purchased or produced by well known methods. The phenyllithium of Flow Scheme A may be prepared by the reaction of lithium metal with bromo or chlorobenzene. The analogous bromo or chlorothiophene or pyridine will produce the analogous thienyllithium or pyridyllithium. A 3-thienyl or 3-pyridyl cyclopent-1-ene may be similarly produced using the analogous thienylmagnesium bromide or pyridylmagnesium bromide. Starting material C2 is well known and available on the market. The arylzinc halides of Flow Scheme C may be produced by treating the arylmagnesium halides with anhydrous zinc halides.

Preferred $R^{a1}$ are selected from the group consisting of bromine, chlorine, fluorine, methyl, ethyl, n-propyl, i-propyl, t-butyl, methoxymethyl, ethoxyethyl, hydroxymethyl, hydroxyethyl, hydroxypropyl, trifluoromethyl, trichloromethyl, methoxy, ethoxy, t-butoxy, trifluoromethoxy, dimethylamino, diethylamino, methylethylamino, methylsulfonyl, ethylsulfonyl, n-propylsulfonyl and phenyl;

Preferred $R^{a2}$ are selected from the group consisting of bromine, chlorine, fluorine, methyl, ethyl, n-propyl, i-propyl or t-butyl.

Preferred $R^b$ are selected from the group consisting of hydrogen, methyl, ethyl, n-propyl, i-propyl, t-butyl, allyl, cyclopropylmethyl, cyclopropyl and cyclohexyl.

Preferred compounds of Formula (I) above have base structures selected from the group consisting of:

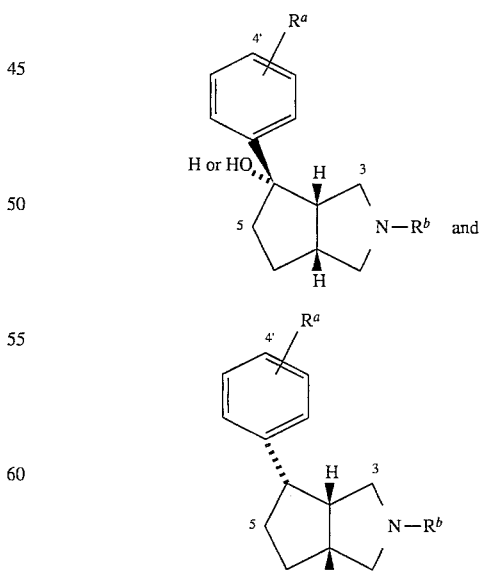

wherein $R^a$ and $R^b$ are simultaneously selected from the group consisting of the groups:

| $R^a$ | $R^b$ |
|---|---|
| 4'-F | Me |
| 3'-methoxy | Me |
| 3'-CF$_3$ | Me |
| 3'-methoxy | cyclopropyl-Me |
| 2',3'-dimethoxy | Me |
| 3',4'-dichloro | Me |
| — | Me |
| 4'-CF$_3$ | Me |
| 3'-CF$_3$ | n-butyl |
| 4'-Cl | Me |
| 2'-Cl | Me |
| 2',5'-dichloro | Me |
| 4'-F | Me |
| 4'-methoxy | Me |
| 3',4'-dimethoxy | Me |
| 4'-i-propyl | Me |
| 4'-Br | Me |
| 4'-SO$_2$Me | Me and |
| 3'-methoxy | cyclopropyl | including the purified enantiomers thereof.

The most preferred compounds of Formula I are:

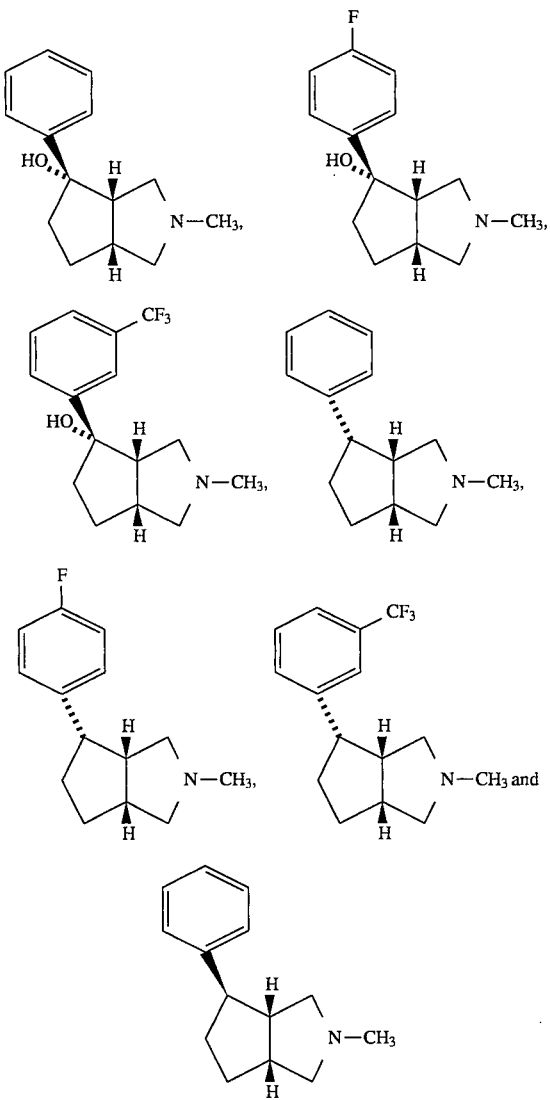

including the racemic mixtures and purified enantiomers of each.

The activity of compounds of the invention as analgesics may be demonstrated by the mouse acetylcholine-bromide induced constriction assay as described below:

Mouse Acetylcholine Bromide-Induced Abdominal Constriction Assay

The mouse acetylcholine-induced abdominal constiction assay, as described by Collier et al. in *Brit. J. Pharmacol Chem. Ther.*, 32: 295–310, 1968, with minor modifications was used to assess analgesic potency of the compounds of formula (I). The test drugs or appropriate vehicle were administered orally (p.o.) and 30 minutes later the animal received an intraperitoneal (i.p.) injection of 5.5 mg/kg acetylcholine bromide (Matheson, Coleman and Bell, East Rutherford, N.J.). The mice were then placed in groups of three into glass bell jars and observed for a ten minute observation period for the occurrence of an abdominal constriction response (defined as a wave of constriction and elongation passing caudally along the abdominal wall, accompanied by a twisting of the trunk and followed by extension of the hind limbs). The percent inhibition of this response to a nociceptive stimulus (equated to % analgesia) was calculated as follows: The % Inhibition of response, i.e., % analgesia is equal to the difference between the No. of control animals response and the No. of drug-treated animals response times 100 divided by the No. of control animals responding.

TABLE I

Mouse Acetylcholine-Bromide Induced Abdominal Constriction Assay

| Compound Number | % Inhibition at 30 mg/kg (route) |
|---|---|
| Cp-1 | 87 (po) |
| Cp-2 | 87 (po) |
| Cp-3 | 87 (po) |
| Cp-4 | 100 (sc) |
| Cp-5 | 87 (po) |
| Cp-6 | 87 (sc) |
| Cp-7 | 100 (sc) |

Based on the above results, invention compounds of formula (I) may be used to treat mild to moderately severe pain in warm-blooded animals such as humans in a manner similar to the use of meperidine hydrochloride by administration of an analgesically effective dose. The dosage range would be from about 10 to 3000 mg, in particular about 25 to 1000 mg or about 100 or 500 mg, of active ingredient 1 to 4 times per day for an average (70 kg) human although it is apparent that activity of individual compounds of the invention will vary as will the pain being treated. Pharmaceutical compositions of the invention comprise the formula (I) compounds as defined above, particularly in admixture with a pharmaceutically-acceptable carrier.

To prepare the pharmaceutical compositions of this invention, one or more compounds of formula (1) or salt thereof of the invention as the active ingredient, is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above.

The pharmaceutically acceptable salts referred to above generally take a form in which the nitrogen of the core ring and/or possibly a nitrogen of a substituent is protonated with an inorganic or organic acid. Representative organic or inorganic acids include hydrochloric, hydrobromic, hydroiodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic or saccharic.

The following Examples illustrate the invention:

EXAMPLES

Procedure A

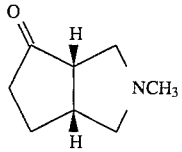

2-Methyl-3aα, 6aα-hexahydrocyclopenta[c]pyrrol-4(1H)-one

A solution of 30.0 g (0.147 moles) N-butoxymethyl-N-methyl-N-trimethylsilylmethylamine, 60 mL of dry $CH_2Cl_2$, 9.5 mL (0.114 moles) of 2-cyclopentene-1-one and 60 drops of 1% TFA in $CH_2Cl_2$ was heated under reflux for one hour. Another 60 drops of 1% TFA in $CH_2Cl_2$ was added in portions at 30 min intervals then refluxed for 45 min. Solid $K_2CO_3$ was added and the reaction was stirred for 30 min. The solution was decanted, washed with $NaHCO_3$ solution, water and brine. It was dried ($K_2CO_3$). The solvent was evaporated in vacuo to give 20 g of an oil. mass spectrum (Cl-$CH_4$) m/z=154 (M+1).

Example 1

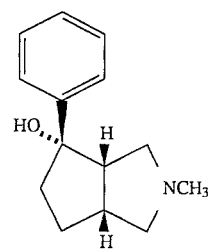

2-Methyl-4α-phenyl-3aα,6aα-octahydrocyclopenta[c]pyrrol-4β-ol.

A solution of 11.8 mL (0.114 moles) of bromobenzene in 75 mL of THF was added dropwise under argon to a solution of 45.6 mL (0.114 moles) of 2.5M n-BuLi in hexanes at –60° C. The mixture was stirred for 2.5 h and a solution of 6.6 g (0.043 moles) of 2-methyl-3aα, 6aα-hexahydrocyclopenta [c]-pyrrol-4(1H)-one in 50 mL of THF was added dropwise. The reaction was stirred for 1.25 h at –78° C. The reaction was poured into water and the organics were washed with water, brine, and dried ($K_2CO_3$). The solvent was evaporated in vacuo to give a brown oil. The oil was flash chromatographed using 90:10:0.5, $CH_2Cl_2$: MeOH: $NH_4OH$ as eluant, then converted to the cyclohexylsulfamic acid salt in acetonitrile to give 3.24 g of the product. mp 158°–161° C. Mass spectrum (Cl-$CH_4$) m/z=218 (M+1). 300 MHz NMR ($Me_2SO$-$d_6$) є 7.5 (Ar, 2H); 7.4 (Ar, 2H); 7.25 (Ar, 1H); 3.5 (m, 1H); 3.3 (s 3H); 3.2 (m, 2H); 3.1 (m, 2H); 2.9–2.8 (m, 2H); 2.75 (s, 3H); 2.3–2.0 (m, 3H); 1.9 (m, 2H); 1.7 (m, 1H); 1.6 (m, 3H); 1.5 (m, 1H); 1.3–1.0 (m, 5H). Anal calcd for $C_{14}H_{19}NO$-$C_6H_{13}NO_3S$: C, 60.58; H, 8.13; N, 7.06. Found: C, 60.46; H, 8.37; N, 7.10.

Example 2

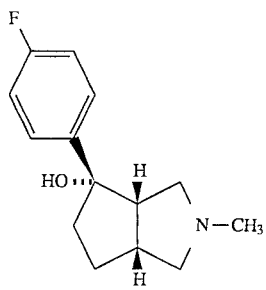

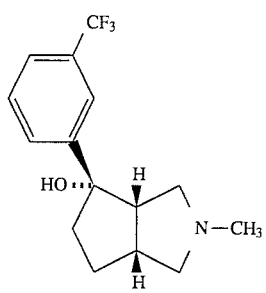

Using the procedure of Example 1 and employing the appropriate arylbromide in place of bromobenzene, the following products were obtained:

4α-(4-Fluorophenyl)-2-methyl-3aα, 6aα-octahydrocyclopenta[c]pyrrol-4β-ol. mp 59°–60° C. mass spectrum (Cl-$CH_4$) m/z=236 (M+1). 300 MHz NMR ($CDCl_3$) δ 7.5 (Ar, 2H); 7.1 (Ar, 2H); 2.95 (d, 1H); 2.9–2.7 (m, 2H); 2.6 (m, 1H); 2.3 (s, 3H); 2.25–2.1 (m, 2H); 2.0–1.8 (m, 3H); 1.7 (m, 1H). Anal calcd for $C_{14}H_{18}FNO$: C, 71.46; H, 7.71; N, 5.95. Found: C, 71.51; H, 7.70; N, 5.98.

4α-(3-Trifluoromethylphenyl)-2-methyl-3aα, 6aα-octahydrocyclopenta[c]pyrrol-4β-ol. mp 54°–56° C. mass spectrum (Cl-CH$_4$) m/z=286 (M+1). 300 MHz NMR (CDCl$_3$), δ 7.85 (Ar, 1H); 7.7 (Ar, 1H); 7.4 (Ar, 2H); 2.9–2.7 (m, 3H); 2.6 (m, 1H); 2.35 (s, 3H); 2.3–2.1 (m, 3H); 2.0–1.85 (m, 3H); 1.7 (m, 1H). Anal calcd for $C_{15}H_{18}F_3NO$: C, 63.15; H, 6.36; N, 4.91. Found: C, 63.09; H, 6.35; N, 4.84.

Example 3

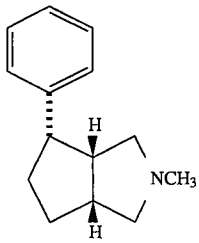

Cp-4

2-Methyl-4β-phenyl-3aα,6aα-octahydrocyclopenta[c]pyrrole.

A solution of 3.24 g (0.015 moles) 2-methyl-4α-phenyl-3aα, 6aα-octahydrocyclopenta[c]pyrrol-4β-ol in 80 mL of acetic acid, and 7.4 mL of 70% perchloric acid were placed in a Parr bottle over 1.5 g 10% palladium on carbon and shaken overnight under 55 psi of hydrogen. The catalyst was filtered off and the flitrate was concentrated in vacuo. The residue was partitioned between diethyl ether and 3N NaOH, the organics were washed with water, brine and dried (K$_2$CO$_3$). The solvent was evaporated in vacuo and the residue was converted to the oxalate salt to give 2.5 g of the product. mp 164°–165° C. mass spectrum (Cl-CH$_4$) m/z= 202 (M+1). 300 MHz NMR (Me$_2$SO-d$_6$) δ 7.35–7.2 (Ar, 5H); 3.6 (t, 1H); 3.2 (m, 2H); 2.85–3 (m, 2H (m, 1H); 2.65 (s, 3H); 2.35 (t, 1H); 2.1–2.0 (m, 1H); 1.85 (m, 1H); 1.7 (m, 1 1.6 (m, 1H). Anal calcd for $C_{14}H_{19}N$-$C_2H_2O_4$: C, 65.96; H, 7.26; N, 4.81. Found: C, 65.66; H, 7.30; N, 4.72.

Example 4

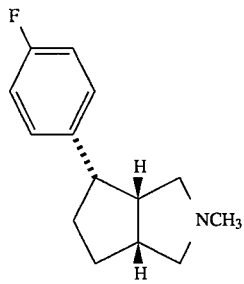

Cp-5

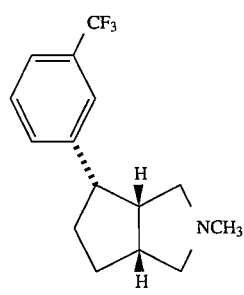

Cp-6

Using the procedure of Example 3 and employing the appropriate 4-aryloctahydrocyclopenta[c]pyrrol-4-ol in place of 2-methyl-4α-phenyl-3aα, 6aα-octahydrocyclopenta[c]pyrrol-4β-ol the following products were obtained:

4β-(4-Fluorophenyl)-2-methyl-3aα,6aα-octahydrocyclopenta[c]pyrrole. mp 170°–171° C. mass spectrum (Cl-CH$_4$) m/z=220 (M+1). 300 MHz NMR (Me$_2$SO-d$_6$) δ 7.3 (Ar, 2H); 7.1 (Ar, 2H); 3.6 (t, 1H); 3.2 (m, 2H); 3.0–2.8 (m, 2H); 2.7 (s, 3H); 2.65 (m, 1H); 2.35 (t, 1H); 2.1 (m, 1H); 1.9 (m, 1H); 1.7 (m, 1H); 1.6 (m, 1H). Anal calcd for $C_{14}H_{18}FN$-$C_2H_2O_4$: C, 62.17; H, 6.52; N, 4.53. Found: C, 62.06; H, 6.48; N, 4.43.

4β-(3-(3-Trifluoromethylphenyl)-2-methyl-3aα, 6aα-octahydrocyclo penta[c]pyrrole. mp 136°–137° C. mass spectrum (Cl-CH$_4$) m/z=270 (M+1). 300 MHz NMR (Me$_2$SO-d$_6$) δ 7.6 (Ar, 4H); 3.6 (t, 1H); 3.4–3.2 (m, 2H); 3.0–2.85 (m, 2H); 2.65 (s, m, 3H, 1H); 2.4 (t, 1H); 2.2-2.1 (m, 1H); 1.9 (m, 1H); 1.75 (m, 1H); 1.65 (m, 1H). Anal calcd for $C_{15}H_{18}F_3N$-$C_2H_2O_4$: C, 56.82; H, 5.61; N, 3.90. Found: C, 56.74; H, 5.50; N, 3.79.

Procedure B

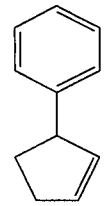

3-Phenylcyclopent-1-ene

A solution of 8 mL of 2M phenylmagnesium bromide in THF was added dropwise to a solution of 32.2 mL (0.016 mole) of 0.5M zinc chloride in THF. A solution of 3.05g (0.024 mole) of 3-acetoxycyclopent-1-ene in 25 mL of dry THF was added, and 321 mg of 1,2-bis(diphenylphosphino)ethane and 462 mg of palladium bis(dibenzylideneacetone) added. The reaction mixture was heated at 40° C. for 18h. The reaction was cooled to room temperature and the solids filtered off. Ether was added, and the organic layer was washed sequentially with saturated ammonium chloride, water, and brine. After drying (MgSO$_4$), the solvent was evaporated in vacuo to give 6 g of a yellow oil. Flash chromatography (SiO$_2$) eluting with hexane gave 760 mg of an oil. Mass spectrum (Cl-NH$_3$) m/z=145 (M+1); 300 MHz NMR (CDCl$_3$) δ 1.68–1.78 (m, 1H); 2.32–2.6 (m, 3H); 3.85–3.96 (m, 1H); 5.72–5.82 (m, 1H); 5.92–6.01 (m, 1H); 7.12–7.38 (m, 5H).

Example 5

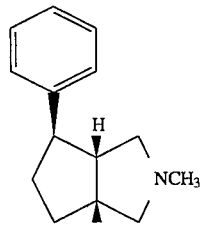

Cp-7

2-Methyl-4α-phenyl-3aα, 6aα-octahydrocyclopenta[c]pyrrole

Distilled diisopropylamine (26.5 mL, 0.202 mole) was added dropwise, under argon, to a solution of 80 mL (0.202 mole) of 2.5M n-butyllithium in hexane and 80 mL of dry THF at −78° C. After the addition was completed, the solution was transferred by cannula to a solution of 5.82 g (40 Mmol) of 3-phenylcyclopent-1-ene and 3.3 g (44 Mmol) of trimethylamino-N-oxide in 80 mL of dry THF at 0° C. The reaction mixture was stirred for 1.75h then poured into water. After extracting with ether, the organic layer was separated and dried ($K_2CO_3$). The solvent was evaporated in vacuo to give an oily residue. Chromatography on the Waters Prep 500 ($SiO_2$) eluting with methylene chloride: methanol: ammonium hydroxide (95:5:0.5) gave 540 mg of an oil. The oil was dissolved in 2-PrOH and 241 mg of oxalic acid added. The salt was recrystallized from methanol to give 306mg of a tan solid, mp 133°–135° C. Mass spectrum (Cl-$NH_3$) m/z=202 (M+1); 300 MHz NMR δ 1.45–1.62 (m,1H); 1.62–1.80 (m, 1H); 2.59–2.72(m, 4H); 2.9–3.09 (m, 2H); 3.09–3.3 (m, 4H); 7.18–7.47 (m, 5H). Anal calcd. for $C_{14}H_{19}N$-$C_2H_2O_4$: C, 65.96; H, 7.27; N, 4.81. Found: C, 65.56; H, 7.50; N, 4.71.

What is claimed is:

1. A compound having analgesic activity of the general formula:

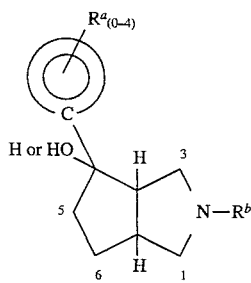

I including the purified stereoisomers and pharmaceutically acceptable salts thereof,
wherein

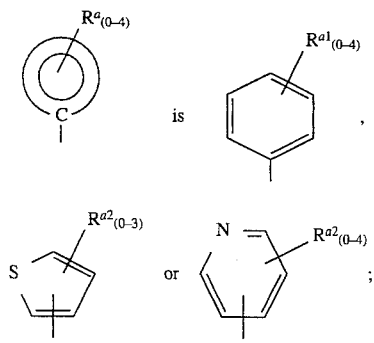

$R^{a1}$ is selected from the group consisting of halogen, $C_{1-4}$alkyl, substituted $C_{1-4}$alkyl (wherein the substituent is $C_{1-4}$alkoxy, hydroxy or perhalo), $C_{1-4}$alkoxy, substituted $C_{1-4}$alkoxy (wherein the substituent is perfluoro), di($C_{1-4}$alkyl)amino, $C_{1-4}$alkylsulfonyl and phenyl;

$R^{a2}$ is selected from the group consisting of halogen or $C_{1-4}$alkyl;

$R^b$ is selected from the group consisting of hydrogen, $C_{1-4}$ alkyl, $C_{1-4}$alkenyl, $C_{1-6}$cycloalkyl methyl and $C_{1-6}$cycloalkyl;

with the proviso that the 3a and 6a hydrogens are cis and where there is a 4-position hydroxy then such is trans to the 3a and 6a hydrogens, and with the proviso that $R^b$ is not hydrogen or $C_{1-4}$alkenyl when the 4-position aryl is cis to the 3a and 6a hydrogens and there is no hydroxy at the 4-position.

2. The compound of claim 1 of the general formula:

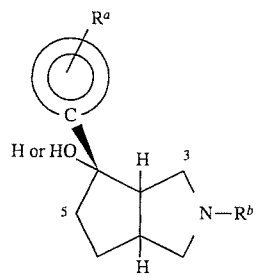

including the purified stereoisomers thereof.

3. The compound of claim 1 of the general formula:

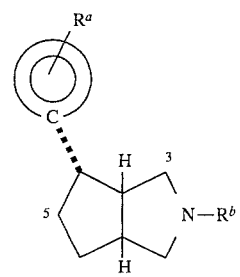

including the purified stereoisomers thereof.

4. The compound of claim 1 wherein:

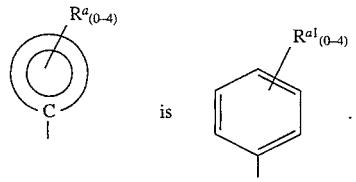

5. The compound of claim 1 wherein:

$R^{a1}$ are selected from the group consisting of bromine, chlorine, fluorine, methyl, ethyl, n-propyl, i-propyl, t-butyl, methoxymethyl, ethoxyethyl, hydroxymethyl, hydroxyethyl, hydroxypropyl, trifluoromethyl, trichloromethyl, methoxy, ethoxy, t-butoxy, trifluoromethoxy, dimethylamino, diethylamino, methylethylamino, methylsulfonyl, ethylsulfonyl, n-propylsulfonyl and phenyl.

6. The compound of claim 1 wherein:

$R^{a2}$ is selected from the group consisting of bromine, chlorine, fluorine, methyl, ethyl, n-propyl, i-propyl and t-butyl.

7. The compound of claim 1 wherein:

$R^b$ is selected from the group consisting of hydrogen, methyl, ethyl, n-propyl, i-propyl, t,-butyl, allyl, cyclopropylmethyl, cyclopropyl and cyclohexyl.

8. The compound of claim 1 wherein said pharmaceutically acceptable salt is a salt made with an acid selected from the group consisting of hydrochloric, hydrobromic, hydroiodic, perchloric, sulfuric, nitric, phosphoric, acetic, proprionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic and a salt made with sacchrine.

9. A compound having a structure selected from the group consisting of:

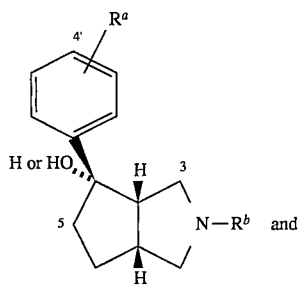

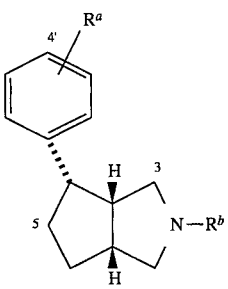

wherein $R^a$ and $R^b$ are simultaneously selected from the group consisting of the groups:

| $R^a$ | $R^b$ |
| --- | --- |
| 4'-F | Me |
| 3'-methoxy | Me |
| 3'-CF$_3$ | Me |
| 3'-methoxy | cyclopropyl-Me |
| 2',3'-dimethoxy | Me |
| 3',4'-dichloro | Me |
| — | Me |
| 4'-CF$_3$ | Me |
| 3'-CF$_3$ | n-butyl |
| 4'-Cl | Me |
| 2'-Cl | Me |
| 2',5'-dichloro | Me |
| 4'-F | Me |
| 4'-methoxy | Me |
| 3',4'-dimethoxy | Me |
| 4'-i-propyl | Me |
| 4'-Br | Me |
| 4'-SO$_2$Me | Me and |
| 3'-methoxy | cyclopropyl | including the purified enantiomers thereof.

10. The compound of claim 1 selected from the group consisting of:

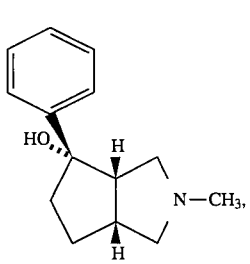
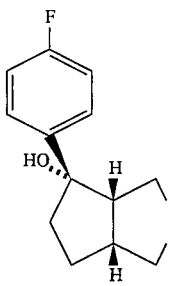

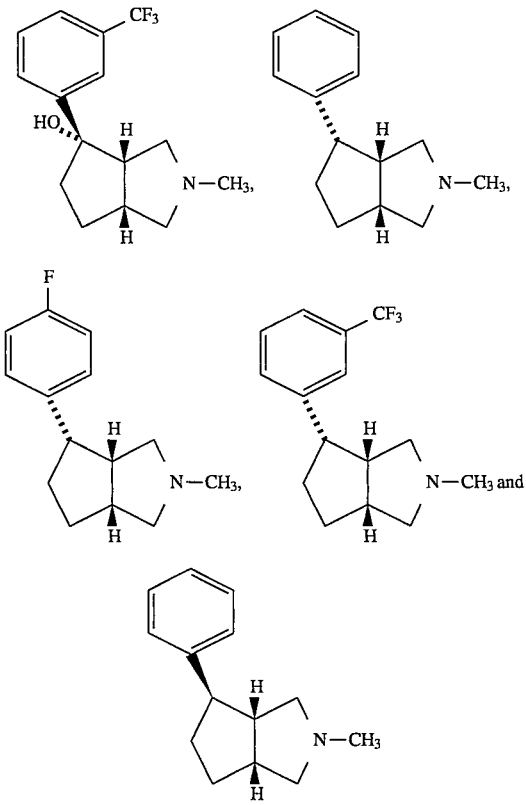

including the racemic mixtures and purified enantiomers of each.

11. A pharmaceutical composition effective as an analgesic in mammals comprising a pharmaceutically acceptable carrier and an effective amount of the compound of claim 1.

12. A method for inducing an analgesic effect in mammals comprising the step of administering an effective amount of the compound of claim 1 in admixture with a pharmaceutically acceptable carrier.

13. A compound selected from the group consisting of:

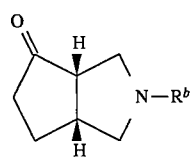

$R^b$ is selected from the group consisting of hydrogen, methyl, ethyl, n-propyl, i-propyl, t-butyl, allyl, cyclopropylmethyl, cyclopropyl and cyclohexyl.

* * * * *